(12) United States Patent
Nauman et al.

(10) Patent No.: US 9,364,584 B2
(45) Date of Patent: Jun. 14, 2016

(54) DEMINERALIZED CANCELLOUS BONE SCAFFOLDS (71) Applicants: Eric A. Nauman, West Lafayette, IN (US); Darryl A. Dickerson, Lafayette, IN (US)

(72) Inventors: Eric A. Nauman, West Lafayette, IN (US); Darryl A. Dickerson, Lafayette, IN (US)

(73) Assignee: Purdue Research Foundation, West Lafayette, IN (US)

(*) Notice: Subject to any disclaimer, the term of this patent is extended or adjusted under 35 U.S.C. 154(b) by 0 days.

(21) Appl. No.: 14/197,823

(22) Filed: Mar. 5, 2014

(65) Prior Publication Data
US 2014/0188242 A1 Jul. 3, 2014

Related U.S. Application Data (62) Division of application No. 12/677,499, filed as application No. PCT/US2008/076176 on Sep. 12, 2008, now Pat. No. 8,702,809.

(60) Provisional application No. 60/972,364, filed on Sep. 14, 2007.

(51) Int. Cl.
A61F 2/28 (2006.01)
A61L 27/36 (2006.01)
A61L 27/38 (2006.01)
A61F 2/30 (2006.01)

(52) U.S. Cl.
CPC .............. A61L 27/3683 (2013.01); A61F 2/28 (2013.01); A61L 27/3608 (2013.01); A61L 27/3645 (2013.01); A61L 27/3843 (2013.01); A61F 2/2846 (2013.01); A61F 2/3094 (2013.01); A61F 2002/2817 (2013.01); A61F 2002/3082 (2013.01); A61F 2002/3085 (2013.01); A61F 2002/30904 (2013.01); A61L 2430/02 (2013.01); A61L 2430/40 (2013.01)

(58) Field of Classification Search
CPC .................... A61F 2/30756; A61F 2002/2839; A61F 2/2846
USPC ................................. 623/51, 61, 63
See application file for complete search history.

(56) References Cited

U.S. PATENT DOCUMENTS

| 277,509 A | 5/1883 | Riegler |
| 277,784 A | 5/1883 | Rider et al. |
| 284,099 A | 8/1883 | Waring |
| 3,772,709 A | 11/1973 | Swanson |

(Continued)

FOREIGN PATENT DOCUMENTS

WO 2008106254 A2 9/2008

OTHER PUBLICATIONS

Anderson et al., "The processing and characterization of animal-derived bone to yield materials with biomedical applications. Part III: material and mechanical properties of fresh and processed bovine cancellous bone," J. Mater. Sci. Mater. Med., 12(4):371, 2001. (Abstract).

(Continued)

Primary Examiner — Brian Dukert
(74) Attorney, Agent, or Firm — Valauskas Corder LLC (57) ABSTRACT The present invention provides a cancellous bone scaffold to use in the replacement or repair of connective tissue such as ligaments and tendons. The cancellous bone scaffold has a fully demineralized segment with at least one adjacent mineralized end segment.

13 Claims, 9 Drawing Sheets (56) References Cited

U.S. PATENT DOCUMENTS

| | | | |
|---|---|---|---|
| 3,875,594 A | 4/1975 | Swanson | |
| 3,886,600 A | 6/1975 | Kahn et al. | |
| 4,627,853 A | 12/1986 | Campbell et al. | |
| 4,759,768 A | 7/1988 | Hermann et al. | |
| 4,871,367 A | 10/1989 | Christensen et al. | |
| 5,092,896 A | 3/1992 | Meuli et al. | |
| 5,133,761 A | 7/1992 | Krouskop | |
| 5,405,400 A | 4/1995 | Linscheid et al. | |
| 5,484,443 A | 1/1996 | Pascarella et al. | |
| 5,824,084 A | 10/1998 | Muschler | |
| 6,090,998 A | 7/2000 | Grooms et al. | |
| 6,200,347 B1 | 3/2001 | Anderson et al. | |
| 6,206,923 B1 | 3/2001 | Boyd et al. | |
| 6,576,017 B2 | 6/2003 | Foley et al. | |
| 6,652,592 B1 | 11/2003 | Grooms et al. | |
| 6,652,593 B2 | 11/2003 | Boyer, II et al. | |
| 6,776,800 B2 | 8/2004 | Boyer, II et al. | |
| 6,855,169 B2 | 2/2005 | Boyer, II et al. | |
| 6,893,462 B2 | 5/2005 | Buskirk et al. | |
| 6,998,135 B1 | 2/2006 | Sunwoo et al. | |
| 7,753,963 B2 | 7/2010 | Boyer, II et al. | |
| 8,372,157 B2 * | 2/2013 | Petersen et al. | 623/23.61 |
| 2001/0020188 A1 * | 9/2001 | Sander | A61F 2/08 623/23.57 |
| 2002/0120346 A1 | 8/2002 | Boyer, II et al. | |
| 2003/0023304 A1 | 1/2003 | Carter et al. | |
| 2004/0215341 A1 | 10/2004 | Sybert et al. | |
| 2004/0243242 A1 * | 12/2004 | Sybert | A61F 2/28 623/17.16 |
| 2005/0136510 A1 | 6/2005 | Hendriks et al. | |
| 2008/0027546 A1 | 1/2008 | Semler et al. | |
| 2008/0058953 A1 | 3/2008 | Scarborough | |
| 2008/0220044 A1 | 9/2008 | Semler et al. | |

OTHER PUBLICATIONS

Gao et al., "Osteochondral Defect Repair by Demineralized Cortical Bone Matrix," Clinical Orthopaedics and Related Research, 427S:S62-S66, 2004.
Gurevitch et al., "Reconstruction of Cartilage, Bone, and Hematopoietic Microenvironment with Demineralized Bone Matrix and Bone Marrow Cells," Stem Cells, 21:588-597, 2003.
Hellmich et al., "Drained and Undrained Poroelastic Properties of Healthy and Pathological Bone: A Poro-Micromechanical Investigation," Transp. Porous. Med., 58:243-268, 2005.
Jackson et al., "Biologic Remodeling after Anterior Cruciate Ligament Reconstruction Using a Collagen Matrix Derived from Demineralized Bone an Experimental Study in the Goat Model," American Journal of Sports Medicine, 24(4):405-414, 1996.
Johnson et al., "The processing and characterization of animal-derived bone to yield materials with biomedical applications: part 1: modifiable porous implants from bovine condyle cancellous bone and characterization of bone materials as a function of processing," J. Mater. Sci. Mater. Med., 11(7):427-441, 2000. (Abstract).
Li et al., "Biological characteristics of demineralized bone matrix: Degradation capacity, interval porosity and adhesion rate," Journal of Clinical Rehabilitative Tissue Engineering Research, 11(31):6121-6124, 2007. (Abstract).
Lu et al., "Anterior cruciate ligament regeneration using braided biodegradable scaffolds: in vitro optimization studies," Biomaterials, 26:4805-4816, 2005.
Mosekilde et al., "Trabecular bone structure and strength-remodelling and repair," J. Musculoskel. Neuron Interact., 1:25-30, 2000.
Pan et al., "Feasibility of the porosity of demineralized and decellularized bone matrix annulus as tissue engineered scaffold of annulus fibrosus disci intervertebralis," Chinese Journal of Clinical Rehabilitation, 10(45):60-61+64, 2006. (Abstract).
Papadopoulos et al., "In Vitro Evaluation of the Mitogenic Effect of Platelet-Derived Growth Factor-BB on Human Periodontal Ligament Cells Cultured with Various Bone Allografts," Journal of Periodontology, 74(4):451-457, 2003.
Tang et al., "Effects of non-enzymatic glycation on cancellous bone fragility," Bone, 40:1144-1151, 2007.
Ten Koppel et al., "Efficacy of Perichondrium and a Trabecular Demineralized Bone Matrix for Generating Cartilage," Plastic and Reconstructive Surgery, 102(6):2012-2020, 1998.
Van Osch et al., "The role of trabecular demineralized bone in combination with perichondrium in the generation of cartilage grafts," Biomaterials, 20:233-240, 1999.
Worth et al., "The evaluation of processed cancellous bovine bone as a bone graft substitute," Clin. Oral Implants Res., 16(3):379-386, 2005. (Abstract).
Worth et al., "Combined xeno/auto-grafting of a benign osteolytic lesion in a dog, using a novel bovine cancellous bone biomaterial," N. Z. Vet. J., 55(3):143-148, 2007.
Yamada, T., "Bone-demineralized bone-bone graft for ligament reconstruction in rats," J. Med. Dent. Sci., 51(1):45-52, 2004.

* cited by examiner

DEMINERALIZED CANCELLOUS BONE SCAFFOLDS

CROSS REFERENCE TO RELATED APPLICATIONS

This application is a divisional of U.S. patent application Ser. No. 12/677,499 filed Nov. 16, 2010, which is a national application of PCT/US2008/076176 filed Sep. 12, 2008, which claims the benefit of U.S. Provisional Patent Application No. 60/972,364 filed Sep. 14, 2007.

BACKGROUND OF THE INVENTION

The present invention relates generally to demineralized bone scaffolds and more particularly to demineralized cancellous bone scaffolds for ligament and tendon repair.

Ligaments provide joint stability, guide joint motion, and play an important role in proprioception while tendons transmit forces up to seven times body weight across joints. In the United States alone, there are 150,000 knee injuries involving the anterior cruciate ligament (ACL) and 23,000 injuries to the anterior talofibular ligament in the ankle each year. In addition, damage to the ligaments and tendons in the glenohumeral joints and the spine often lead to long-term musculoskeletal disorders.

Reconstruction with a soft tissue autograft is the most prominent surgical technique for repair of soft connective tissue ruptures. Autografts are preferred due to their biocompatibility and lowered risk for disease transmission. However, graft availability is quite limited and autologous tissue transfer requires the sacrifice of normal tissues. Additionally, in many cases, use of autografts does not regenerate the normal tissue structure, particularly at the interface between the soft connective tissue and the bone. Soft connective tissues join with bone through a complex and distinct interface with our layers. The first is the connective tissue proper, or midsubstance, which consists mostly of a type I collagen matrix. The midsubstance inserts into a layer of fibrocartilage mainly composed of type II collagen rich with proteoglycans. This layer transitions into calcified fibrocartilage layer. The final region is subchondral bone, which contained a mineralized type I collagen matrix. The junction between bone and soft connective tissue has controlled heterogeneity, permitting a gradual manner of load transmission from the hard tissue to the soft tissue in a manner hypothesized to minimize stress and strain concentrations. Prior studies using autografts have shown that using the soft connective tissue proper as the sole graft does not lead to strong biological integration and the re-establishment of the native bone-soft tissue interface. Without such integration, mechanical stability is limited at the joint and the lack of integration can produce higher rates of graft failure. In order to restore the physiological structure and function of the tissue, new strategies must be developed for the treatment of soft connective tissue ruptures.

Tissue engineering has emerged in the past twenty years a promising strategy for soft connective tissue repairs. There have been a number of reports on the use of tissue engineering techniques to regenerate ligaments and tendons. However, most of these studies focus on the midsubstance region and fail to address the regeneration of the interface. To date, collagen fibers, silk fibers, collagen gels and synthetic polymer scaffolds have been utilized to replace the soft tissue portion of the ligament or tendon. One example is a composite collagen fiber-collagen gel scaffold seeded with fibroblasts that does not degrade in vitro and matches many of the mechanical properties of normal ligaments. Unfortunately for many tissues, especially those in the musculoskeletal system, matching the mechanical properties is not sufficient. In order to transmit loads, the construct must successfully integrate with the host tissue and revascularize, processes that are largely governed by the construct's permeability.

Alternatively, bone implants for repairing damaged ligaments and tendons have been made from cortical bone. Examples of such implants are disclosed in U.S. Pat. Nos. 6,090,998 and 6,652,592 (incorporated herein by reference). However, cortical bone is dense with a maximum pore size of 50 µm and implants made from cortical bone do not revascularize to any appreciable extent.

There are a number of design requirements that, once met, may optimize the development of a tissue engineered solution for soft connective tissue rupture. This design requires a biocompatible scaffold that has the mechanical properties to withstand the loading environment. Ideally, the scaffold would be porous to allow more rapid cell incorporation along the surface and through its thickness. The porosity should ensure that cell viability through the thickness is not dependent on vascularization. Tissue ingrowth is vital, but, specifically for this application, the ingrowth must be accompanied by biological integration, so that the normal interface is reformed. Cell behavior is expressly controlled by the interaction with its extracellular environment, in particular the biomaterial surface. The scaffold must guide cells to regenerate of the entire tissue and not simply the soft connective tissue midsubstance.

As can be seen, there is a need for a bone implant or construct that has structural integrity and can easily be integrated into bone and revascularize. It would be desirable if the bone implant allowed for easy attachment to bone and could be custom sized for different applications and patients.

SUMMARY OF THE INVENTION

In one aspect of the present invention there is provided a cancellous bone scaffold comprising at least one mineralized end segment and a fully demineralized segment adjacent to the mineralized end segment. The cancellous bone scaffold may comprise only one mineralized segment or two mineralized end segments. The fully demineralized bone segment may have a calcium content of from about 0 wt % to about 2 wt %. The number of mineralized end segments will depend on the application of use for the cancellous bone scaffold. For example, but not limited to, a cancellous bone scaffold with a single demineralized end segment may be used for tendon repair wherein a scaffold with two mineralized end segments may be used for ligament repair. There may also be a partially demineralized bone segment between the mineralized end segment and the fully demineralized segment.

In another aspect of the present invention, a method is provided for replacing or augment damaged tissue, the method comprising attaching the cancellous bone scaffold to the attachment area of the tissue, wherein the damaged tissue is a ligament, a tendon, cartilage, a intervertebral disk or a bone growth plate.

These and other features, aspects and advantages of the present invention will become better understood with reference to the following drawings, description and claims.

DETAILED DESCRIPTION OF THE INVENTION

The following detailed description is of the best currently contemplated modes of carrying out the invention. The description is not to be taken in a limiting sense, but is made merely for the purpose of illustrating the general principles of the invention, since the scope of the invention is best defined by the appended claims.

The present invention provides a cancellous bone scaffold comprising at least one mineralized end segment and a fully demineralized segment adjacent to the mineralized end segment. Cancellous bone scaffolds have an advantage over the prior art scaffolds of cortical bone in that it can vascularize much more easily. Cortical bone is the dense surface layer of the bone having little vascularization. In contrast, cancellous bone is a spongy material that makes up the bulk of the interior of bones. Compared to cortical bone it has a low density and strength, but very high surface area. These differences are result in demineralized bone where cancellous bone comprises pores with diameters of about 100 microns to 2 mm while, in contrast, cortical bone has a maximum pore size on the order of 50 microns.

The present invention also provides methods for using the cancellous bone scaffolds. They may be used in ligament, tendon, cartilage and growth plate repair. The mineralized bone segment can be inserted into or otherwise anchored to the bone at the point of repair while the demineralized segment is anchored to adjacent tissue if necessary. The cancellous bone scaffold provides a scaffold for tissue growth and regeneration to repair the damaged tissue.

In one embodiment of the cancellous bone scaffold of the present invention comprises at least one mineralized end segment adjacent to a fully demineralized segment. In one illustrative embodiment, the cancellous bone scaffold comprises two mineralized end segments. A scaffold with two mineralized end segments may be used, for example, in the repair or replacement of damaged ligaments. When ligaments are replaced or repaired, there is usually attachment to bone on either end. In an alternate illustrative embodiment, the cancellous bone scaffold has one mineralized end segment adjacent to the fully demineralized segment. A scaffold with one mineralized end segment may be used, for example, for repairing tendons where one end of the scaffold is attached to bone and the other end sutured to the tendon.

The fully demineralized segment of the scaffold may have a calcium content of from about 0% to about 2%. The scaffold may further comprise a partially demineralized bone segment between the mineralized segment and the demineralized bone segment. A partially demineralized bone segment may have a calcium content from about 2% to about 10% calcium. The partially demineralized segment may be significantly smaller than either the fully demineralized or the mineralized segments.

The cancellous bone scaffold may be an autograft, an allograft or a xenograft. If the scaffold is a xenograft it may be from, by way of non-limiting example, ovine, porcine or bovine bone. The cancellous bone may be taken from any bone where it is available in the size required. In one illustrative embodiment, the cancellous bone is vertebral cancellous bone. After being obtained from bone, the marrow is removed from the cancellous bone. The portion of cancellous bone may then be shaped. Alternatively, the cancellous bone may be shaped before removal of the marrow. The cancellous bone portion may be shaped into any shape desired for the scaffold. It will be appreciated that the shape of the scaffold will depend on the application and where in the body the scaffold will be placed. Non-limiting examples of scaffold shapes may be a sheet, a rectangular block, a cylinder, a dog-bone shape or a parallelepipeds. Although these shapes are given as an example, it is well within the knowledge of the skilled artisan to design any shaped scaffold necessary without undue experimentation. The size of the scaffold may also vary according to the desired use of the scaffold. In an illustrative embodiment, the scaffold may have a thickness of about 0.1 mm to about 15 mm or about 0.5 mm to about 10 mm, although it may be smaller or larger as required. For example, if the scaffold is being used to repair the ankle, the scaffold may be smaller than 0.55 mm. Alternatively, if the scaffold is being used to repair an articular cartilage defect in the knee, the scaffold may be larger in size.

It will be appreciated that the cancellous bone scaffold of the present invention may be appropriately fashioned for a wide diversity of applications. For example, a cancellous bone scaffold of this invention may be applied to repair of ligaments, tendons, cartilage or growth plates in the hand, elbow, knee, foot, ankle or any other anatomical location as needed. Furthermore, the scaffold of the present invention may be applied to replace or repair any of a variety of joints. Methods and implant shapes known in the art for joint replacement, (see, for example U.S. Pat. No. 4,871,367; Des. 284,099; Des. 277,784; Des. 277,509; U.S. Pat. Nos. 3,886,600; 3,875,594; 3,772,709; 5,484,443; 5,092,896; 5,133,761; 5,405,400; and 4,759,768; all of which are herein incorporated by reference for their teachings of various considerations applicable to joint prosthetic implants), may be fashioned according to and replaced by the implant of the instant disclosure.

The fully demineralized segments of the cancellous bone scaffold may be formed by any method known in the art. It is well known how to prepare fully demineralized bone and any of those methods may be used. The end segment(s) that will remain mineralized must be masked before demineralization. Any method or substance may be used to mask the bone that is resistant to demineralization conditions and may be readily removed after demineralization. Alternatively, the bones may be masked with a material that is biologically and physiologically compatible and therefore does not need to be removed after demineralization. While the methods of the prior art use rubber gaskets, stoppers and tape to mask the portions that are to remain mineralized, it was found that these methods are undesirable for the present invention as they allow for some demineralization. For the cancellous bone scaffold of the present invention it is important that the segment to remain mineralized retain as much of its mineral content as possible. To achieve this, the end segment(s) remaining mineralized may be masked with wax or with a polymer such as liquid bandage, which is a polycyanoacrylate polymer. In one illustrative embodiment, the polymer is any polymer that may be removed with acetone or ethanol.

In the present invention, the orientation of the mineralized-demineralized interface of the cancellous bone scaffold may be controlled, allowing for the cancellous bone scaffold to form direct or indirect insertions according to application it is to be used for. The structural interface at which the fibers of the tendon insert into calcified bone matrix is known as an insertion. The insertion may be direct or indirect. Direct insertion shows four distinct zones: ligament, unmineralized fibrocartilage, mineralized fibrocartilage and bone. Indirect insertions contain collagen fibers which blend with periosteal collagen fibers, which in turn are anchored to the adjacent bone without a fibrocartilage layer. Indirect insertions contain Sharpey's fibers, which are collagen fibers that are continuous from ligament to bone. Direct insertions are typically associated with long tendons inserting into small areas of bone, while indirect insertions are usually short tendons inserting into a large area.

The present invention provides cancellous bone scaffolds where the mineralized segment may be positioned, by way of non-limiting example, at the long end of the scaffold. This may be desirable for applications where there is a direct insertion into the bone. Alternatively, the mineralized segment may be on a lateral face of the scaffold, allowing for either an angled direct insertion into bone or an indirect insertion.

The cancellous bone scaffolds of the present invention may be treated to increase the strength of the scaffold. For collagenous structures, crosslinking provides greater mechanical strength and a degree of resistance to proteolytic enzyme degradation, increasing the in vivo lifetime of the cancellous bone scaffolds. The cancellous bone scaffolds may be crosslinked, either chemically or mechanically. Crosslinking the cancellous bone scaffold may substantially increase the mechanical integrity of the scaffold, without substantially altering the cytocompatibility of the scaffold. Additionally, both the physical and chemical crosslinking methods may be biologically compatible. A non-limiting examples of physical crosslinking may be dehydrothermal crosslinking or crosslinking by exposure to gamma radiation or ultraviolet radiation. Physical crosslinking methods of proteinaceous material such as the cancellous bone scaffolds are well known in the art.

Alternatively, the cancellous bone scaffold may be chemically crosslinked. Functional groups that specifically react with amines may be, but not limited to, aldehydes, N-hydroxysuccinimide (NHS), isocyanate, epoxide and acrylate. The collagen material of the cancellous bone scaffold is known to comprise lysine residues that may be crosslinked. Functional groups that are non-selective may be, but not limited to, active esters, epoxides, azides, carbonylimidazole, nitrophenyl carbonates, tresylate, mesylate, tosylate and isocyanate. Other agents may also be employed for chemically crosslinking the cancellous bone scaffold, including, but not limited to, carbodiimides, genipin, aldehydes such as glutaraldehyde and formaldehyde, acyl azide, poly-epoxy compounds, butanediol diglycidyl ether, dye mediated photooxidation or tannic acid. Chemical crosslinking agents of collagen-based material such as the cancellous bone scaffolds are well known in the art.

A mixture of crosslinking agents may be used. The choice of crosslinking agent may depend on the amount of crosslinking desired, although this may also be controlled by controlling the time of the crosslinking reaction and/or by controlling the concentration of the crosslinking agent. It will be appreciated that the mechanical properties of the cancellous bone scaffold could be tailored specifically for a given application by altering crosslinking conditions, including length of time, temperature, and chemical reaction mixture concentrations.

Demineralized cancellous bone is osteoinductive and is most often employed to help in the regeneration of bone. For utilization in ligament and tendon repair, the osteoinductivity may be removed from the cancellous bone scaffold. Methods are known in the art for removing the osteoinductivity such as, but not limited to, peroxide.

The mineralized segment may be further machined to comprise a groove, an external thread, an internal thread, a tooth-like serration or a driver head or any other shape or form that allows for attachment to bone. The recipient bone may then be machined in a complimentary fashion so that the cancellous bone scaffold may be inserted into the recipient bone.

The cancellous bone scaffold may further comprise cells, pharmaceuticals, antibiotics, growth factors, collagen gel or mixtures thereof. It is contemplated that any compound or biologic that helps in healing and integration of the scaffold may be added. Non-limiting examples of cells that may be added are fibroblasts, chondrocytes, osteoblasts or mixtures thereof. It will be appreciated that fibroblasts may be added to the demineralized segment of the cancellous bone scaffold to help regenerate ligaments or tendons, while the osteoblasts may be added to the mineralized segment to allow greater integration with the recipient bone. Alternatively, the cancellous bone scaffold may comprise plasma or platelet rich plasma. Platelet rich plasma contains a number of cells and growth factors that have been shown to aid in the growth and integration of bone, cartilage and connective tissue implants. In yet another alternative example, the cancellous bone scaffold may further comprise adult stem cells. Non-limiting examples of adult stem cells are bone marrow stem cells and adipose-derived stem cells.

The cancellous bone scaffold of the present invention may be useful in treating injuries involving interfaces within connective tissues. The major applications include repair of ligaments, tendons, and cartilage. Ligaments are dense bands of connective tissue composed primarily of type I collagen that connect bones to other bones. Ligaments function as motion guides and joint motion restrictors. At all articulating joints (neck, spine, shoulder, elbow, wrist, hip, knee, ankle) in the body, these tissues are placed under constant dynamic loading. An injury known as a sprain results when the ligaments are stretched, and in some cases, stretched severely enough to be torn. While in some cases, ligament tears can heal on their own, other cases show a lack of inherent healing capacity. If left untreated or if treated improperly, ligament tears can lead to chronic disability including arthritis at the affected joint.

Tendons, like ligaments, are dense collagenous tissues found at every articulating joint in the body. Tendons, however, connect muscles to bone, allowing the force produced by the muscles to be translated into motion. When overloaded, tendons are at risk for tearing and in some cases require surgical replacement to return joint motion and prevent muscle atrophy.

The present invention provides methods for replacing or augmenting damaged fibrous connective tissue which may comprise attaching the cancellous bone scaffold as described above to the attachment area of the fibrous connective tissue. In one embodiment, a method for repairing a ligament with a cancellous bone scaffold comprising a first and a second mineralized end segment each adjacent to a fully demineralized segment is provided where the method may comprise inserting one mineralized end segment of the cancellous bone scaffold into a first bone portion and inserting the second mineralized end into a second bone portion. The first and second bone portions may be located on individual bones or may be in different areas of the same bone. The insertion may be direct or indirect. Additionally, if the ligament being replaced is long, it may be desirable to attach the demineralized segment of the cancellous bone scaffold to a tendon, muscle, another bone portion or any other available anchor point selected by the skilled artisan.

In another embodiment, a method for repairing a tendon with a cancellous bone scaffold comprising a mineralized end segment each adjacent to a fully demineralized segment is provided where the method may comprise inserting the mineralized end segment of the cancellous bone scaffold into a bone portion. The insertion may be direct or indirect. The demineralized segment of the cancellous bone scaffold may be attached to muscle. The demineralized portion may additionally be attached to a ligament, bone or any other available anchor point selected by the skilled artisan to further support and immobilize the scaffold while new tissue is being formed.

The cancellous bone scaffold may also be utilized for more complex orthopaedic interface problems, including injury at the bone growth plate in youth and intervertebral disk repair in the spine. The methods for repairing a bone growth plate or intervertebral disks in the spine may be similar to those for repair of ligaments or tendons. For example, a method for repairing an intervertebral disk in a spine with a cancellous bone scaffold comprising a mineralized end segment each adjacent to a fully demineralized segment may method comprise inserting the mineralized end segment of the cancellous bone scaffold into a vertebra. The insertion may be direct or indirect. The fully demineralized segment is then placed between the vertebra to which it is attached and an adjoining vertebra. As it heals, the fully demineralized segment of the cancellous bone scaffold may be replaced by regenerated disc tissue, providing cushioning between the vertebrae.

In another embodiment, methods are provided for repairing cartilage using the cancellous bone scaffold of the present invention. Cartilage is a connective tissue found mainly on the surface between articulating bones. Degradation of cartilage can result in diseases such as, but not limited to, arthritis, which results from the grinding of bone at joints due to cartilage degradation. In repairing damaged cartilage, proper anchorage requires growth into the subchondral bone to properly integrate and restore function. A method for repairing cartilage with a cancellous bone scaffold comprising a first and a second mineralized end segment each adjacent to a fully demineralized segment is provided where the method may comprise inserting one mineralized end segment of the cancellous bone scaffold into a first bone portion at a joint and inserting the second mineralized end into a second bone portion at the same joint. Alternatively, if cartilage is only desired on the end of a single bone, the method may comprise inserting the mineralized end segment of the cancellous bone scaffold into a bone portion. The insertion may be direct or indirect in either method. The fully demineralized segment may further comprise chondrocytes to aid in the formation of cartilage.

It should be understood, of course, that the foregoing relates to exemplary embodiments of the invention and that modifications may be made without departing from the spirit and scope of the invention as set forth in the following claims.

EXAMPLES

Materials and Methods

Cancellous Bone Preparation:

Samples were prepared from bovine cancellous bone harvested from the vertebral bodies of commercially obtained steers (Parrett's Meat Processing, Flora, Ind.). Residual tissue soft tissue was removed from the vertebral bodies. Using a diamond saw, the samples were sectioned into 3 mm×3 mm×40 mm blocks. Small scaffolds were created by cutting these samples to a height a 2 mm. All samples were washed in a detergent solution to remove fat and marrow from the intertrabecular spaces. Samples were subsequently washed well in deionized water for 4 hours. Samples were defatted by soaking in acetone for 12 hours.

Demineralization Time:

Small scaffolds were placed in a volume (50 mL per gram bone) of special demineralizing solution (3.2 M HCl, 1.9 mM ethylene diamine tetraacetic acid) for 0, 1, 4.5 and 24 hours to determine the minimum amount of time needed to fully demineralize the samples. Following demineralization, the samples were washed thoroughly in deionized water.

Sample Protection:

Small undemineralized scaffolds were covered with a solution of 0.2% Benzethonium Chloride, 0.75% Dyclonine Hydrochloride, and 8-hydroxyquinoline and allowed to dry. Samples were then placed in the special demineralizing solution for the minimum demineralization time, then rinsed thoroughly in deionized water. Samples were imaged before and after placement in demineralizing solution using micro-computer tomography ($\mu$CT).

Osteoinductivity Removal Treatment:

In order to successfully use demineralized bone in soft tissue regeneration applications, it is important to remove the inherent osteoinductivity. The effects of such treatment on the cell-matrix interactions were determined. After cleaning and demineralization was complete, samples were soaked in hydrogen peroxide for 12 hours. Scaffolds were placed into 24 well plates and each scaffold suspended in a cell solution containing $1\times10^5$ adipose stem cells (ASC). The cells were allowed settle onto the scaffold for 12 hours in a humidified 37° C./5% $CO_2$ incubator. After this period, the scaffolds were transferred to another 24 well plate. Scaffolds from all four groups, untreated with and without ASC and peroxide treated with and without ASC, were cultured for 5 days for short term culture and 30 days for long term culture. Full media exchange was performed every other day.

Crosslinking:

After the pre-treatment to remove osteoinductive properties from the sample, the demineralized bone scaffolds were separated into 3 groups: uncrosslinked, physically crosslinked, and chemically crosslinked. Physical crosslinking was achieved using dehydrothermal (DHT) treatment. Samples were DHT crosslinked by placing them in an oven at 110° C. under 100 mTorr for 2 days. Chemical crosslinking was performed using 1-ethyl-3-(3-dimethyl aminopropyl) carbodiimide (EDC) and Nhydroxysuccinimide using a protocol derived from Pieper et al. (Biomaterials, 1999. 20(9): p. 847-58). Briefly, scaffolds were soaked for 0.5 h in 50 mM 2-morpholinoethane sulphonic acid (MES, Fluka Chemie AG, Buchs, Switzerland). Samples were then placed in 50 mM MES containing 33 mM EDC (Fluka Chemie AG) and 6 mM NHS (Fluka Chemie AG). After 4 hrs, the samples were washed twice in 0.1 M $Na_2HPO_4$ for 1 h. Finally, the samples were washed with 1 M NaCl and 2 M NaCl for 2 h and 1 day. The samples were then thoroughly washed in deionized water. Long samples were used for tensile testing, while small samples were used to determine cell proliferation.

Analytical Methods

Calcium Content:

Scaffolds were dried at room temperature for 24 hrs and weighed using an analytical balance. Each scaffold was placed into 6 mL of 2 M HCl for 24 hrs. Residual calcium content was measured using Inductively Coupled Plasma Atomic Emission Spectroscopy (ICP-AES). Calcium concentrations in solutions were calculated by using standards of calcium chloride in 2 M HCl. The calcium content of each scaffold was normalized to the total dry weight of the scaffold.

Relative Cell Number Quantification:

Cell seeded scaffolds were covered with a 0.9% solution of Triton X-100 in order to release the intracellular content. CytoTox 96 Non-Radioactive Cytotoxicity Assay (Promega Corporation, Madison, Wis.) was then used to measure lactate dehydrogenase (LDH) activity. The total LDH activity was compared across groups to get a relative measure of cell number.

Mineral Assessment:

Micro-computed tomography (μCT) was used to image scaffold structures and quantify mineral content. μCT images were taken a μCT imaging system (Scanco Medical μCT 40, Bassersdorf, Switzerland) that provided an isotropic resolution of 16 μm. Energy was set to 40 kVp and integration time was 200 ms.

Mechanical Testing:

Long samples from each peroxide treatment group and each crosslinking group were tested in uniaxial tension to obtain load-deformation curves. Samples were hydrated in phosphate buffered saline for at least 4 hours prior to the test. Each sample was mounted between rubber with an adhesive to ensure grip attachment. Samples were loaded into the aluminum clamps of a custom designed mechanical testing unit consisting of a linear actuator and a 111 N load cell. The gauge length was set to be 30 mm between the clamps. Device operation and data acquisition were controlled with LabView software (National Instruments, Austin, Tex.). The samples were loaded to failure at a 10%/s strain rate. 5 Curves of the nominal stress vs. Green's strain were calculated from the load-deformation output. The ultimate tensile stress, strain at failure, and tangent modulus were calculated from these curves. Postprocessing of data considered strain to be zero when the sample was minimally loaded to 0.1 N, less than 1% of the ultimate load of the weakest sample.

Results

Figure 1:
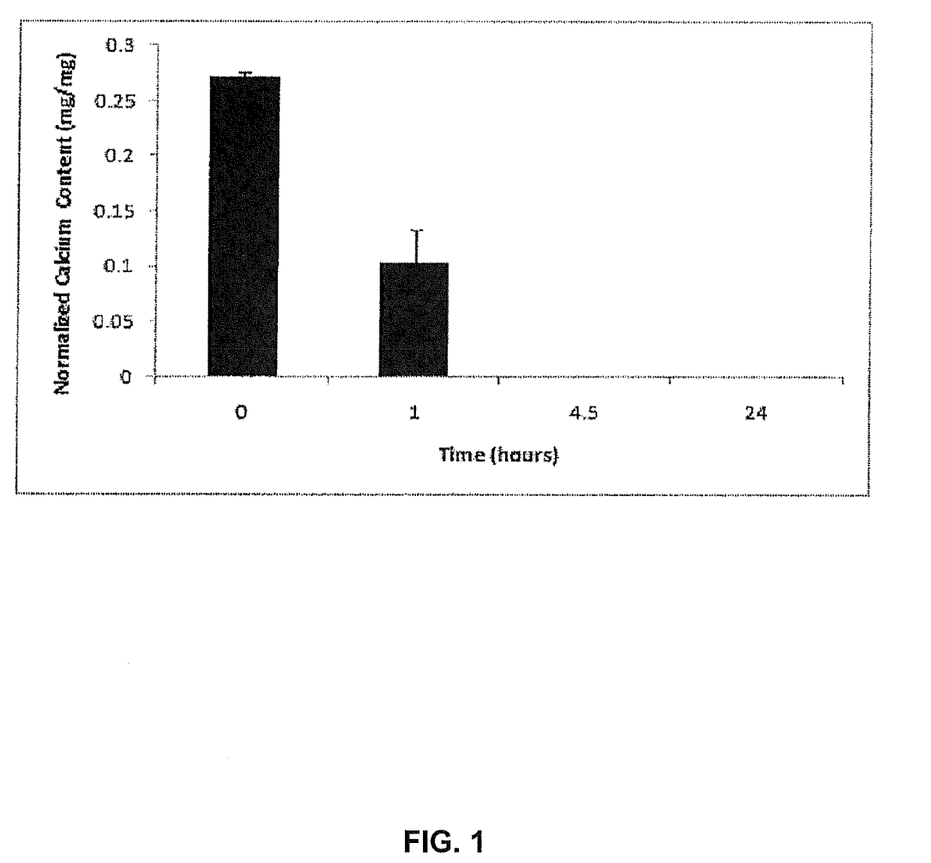
FIG. 1 is a bar graph showing the calcium concentration in cancellous bone samples as a function of time in a demineralizing solution.

Minimum Demineralization Time:

The first step in developing a composite scaffold from cancellous bone is to determine the optimum process for demineralization. Samples were exposed to demineralizing solution for varying periods of time and used ICP-AES to assay for calcium content as a function of sample mass following treatment. As illustrated in FIG. 1, most of the mass loss occurs within the first hour in the demineralization solution, and that the samples are completely demineralized after 4.5 hours of treatment. Each time point is the average of three samples.

Figure 2A:
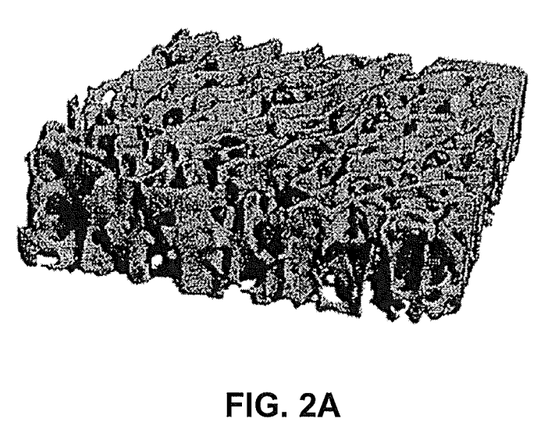
FIG. 2A is a μCT image of a small cancellous bone scaffold protected with a polymer coating before exposure to a demineralizing solution for 4.5 hrs.
Figure 2B:
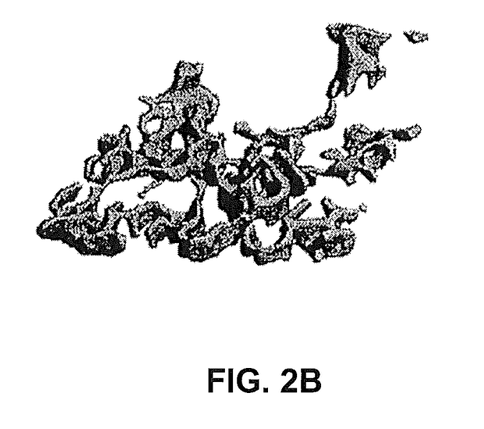
FIG. 2B is a μCT image of a small cancellous bone scaffold protected with a polymer coating after exposure to a demineralizing solution for 4.5 hrs.

Mineral Protection:

In order to create a contiguous scaffold with mineralized and demineralized sections, samples were coated with a polymer to protect the sections from being demineralized within the minimum 4.5 hours of exposure time. μCT scans were taken before and after the demineralization process to determine the efficacy of the treatment (FIGS. 2A and 2B). The protective polymer coating was able to retain 5.36%±1.54% of the mineral within the scaffolds (FIG. 2A). Thus, some of the mineral within the sample can indeed be protected from the action of the demineralizing solution.

To determine if using such a coating could produce a scaffold with mineralized and demineralized sections, the ends of long cancellous bone samples were coated in the polymer solution and placed in demineralizing solution for the minimum treatment time. The resulting structure was a cancellous bone-soft tissue-cancellous bone scaffold.

Figure 3:
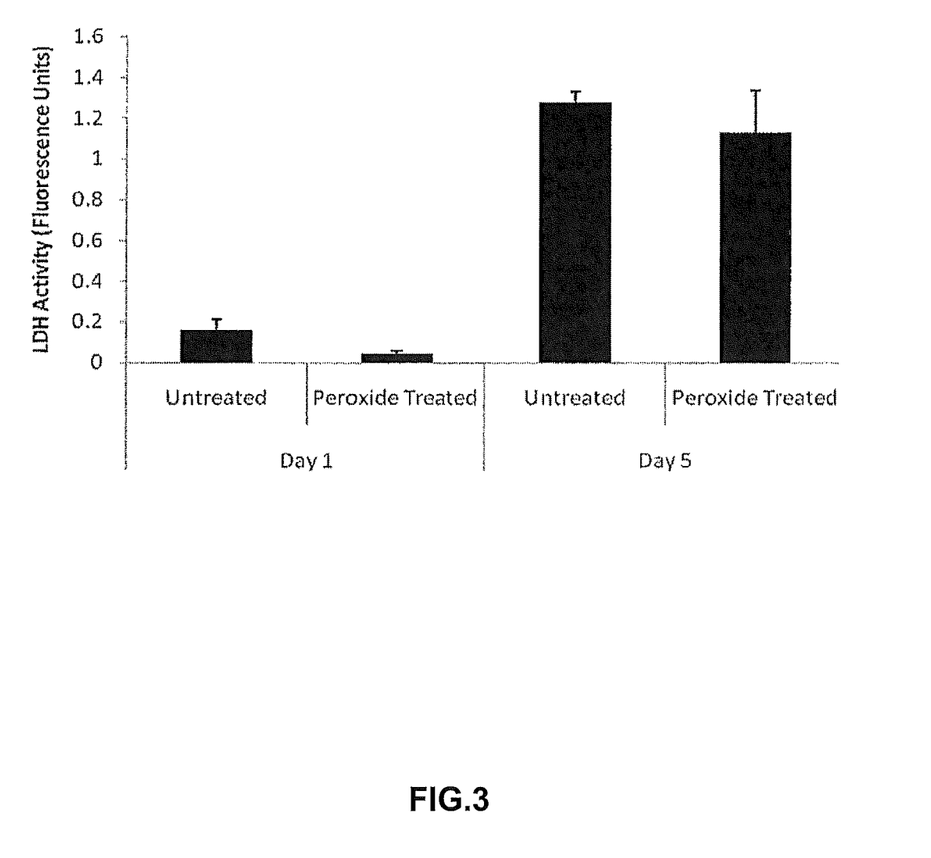
FIG. 3 is bar graph showing the relative number of ASC on demineralized cancellous bone scaffolds as determined by lactate dehydrogenase (LDH) for up to five days in culture.

Cell-Biomaterial Interaction:

Demineralized bone is a well known osteoinductive agent. However, for this application, it is critical that the osteoinductivity of the bone be removed to promote the regeneration of soft tissue in the demineralized region of the scaffold. Previous studies have shown peroxide treatment to be effective in the removal of osteoinductivity. The effect of the exposure of demineralized bone to peroxide on the cell attachment and proliferation on the scaffolds was explored. ASC attachment to the peroxide treated scaffolds was slightly, but not significantly less than attachment on untreated scaffolds (FIG. 3, day 1). Over time, proliferation proceeded as normal and was not inhibited by peroxide treatment (FIG. 3, day 5). After 30 days in culture, μCT analysis showed no bone on the demineralized scaffolds indicating that the demineralized as treated for this experiment lacked osteoinductive properties. The data represent an average of four samples.

Figure 4A:
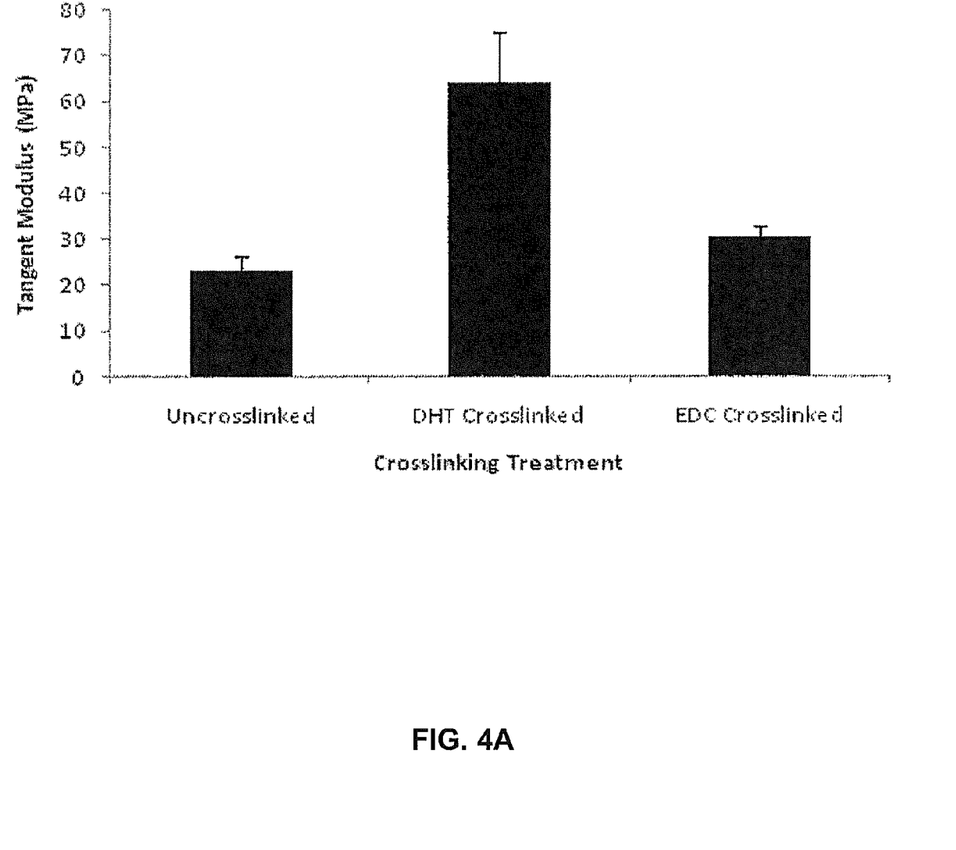
FIG. 4A is a bar graph showing the tangent modulus of crosslinked and uncrosslinked demineralized cancellous bone scaffolds.
Figure 4B:
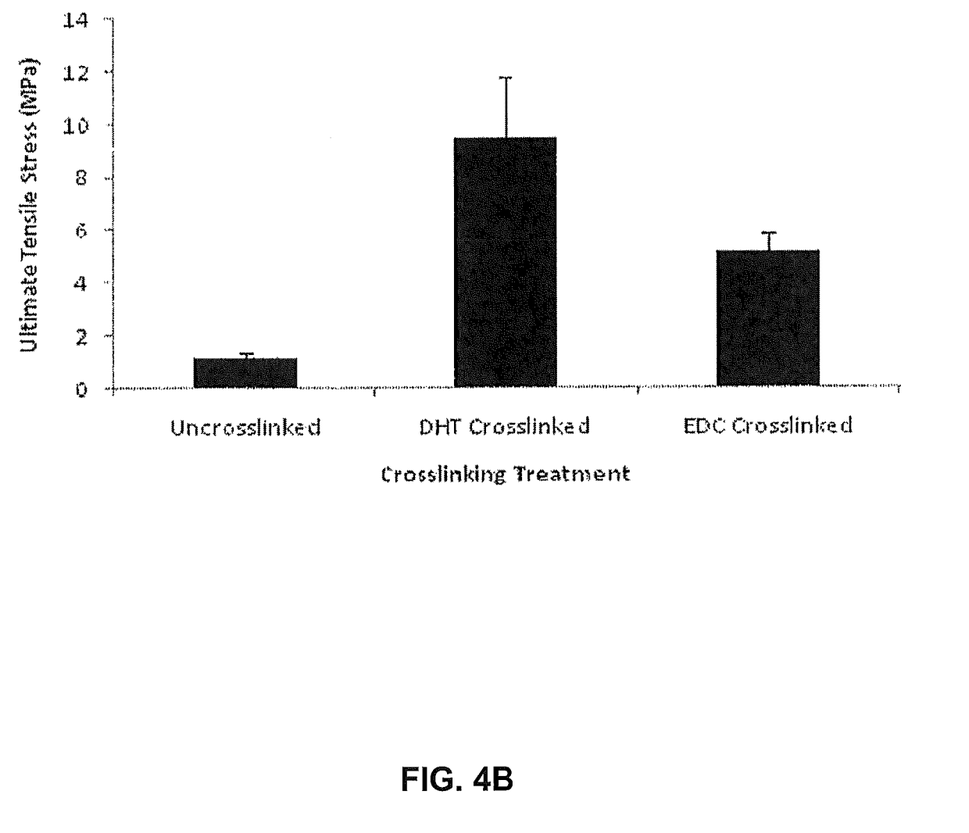
FIG. 4B is a bar graph showing the ultimate tensile strength of crosslinked and uncrosslinked demineralized cancellous bone scaffolds.
Figure 4C:
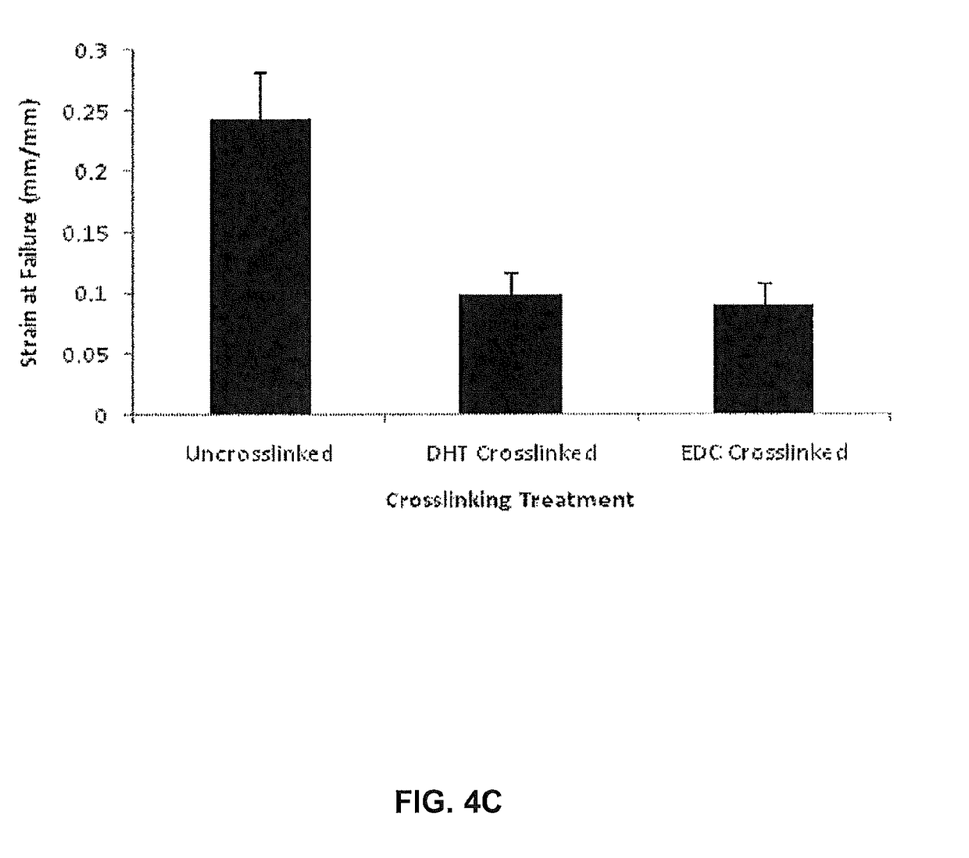
FIG. 4C is a bar graph showing the strain at failure of crosslinked and uncrosslinked demineralized cancellous bone scaffolds.

Mechanical Properties:

To characterize the mechanical properties of the demineralized cancellous bone, long scaffolds treated with peroxide were loaded under uniaxial tension until failure. The stress-strain curves roughly followed the characteristic J shape of soft connective tissue. The tangent modulus (FIG. 4A), ultimate tensile strength (UTS; FIG. 4B) and the strain at failure (FIG. 4C) were captured from the collected data. The tangent modulus was calculated as the slope of the linear section of the curve. Material properties of the scaffold, particularly modulus, were notably weaker than that of normal connective tissues. As such, to strengthen the scaffolds, DHT and EDC crosslinking treatments were performed. Tangent modulus and UTS were enhanced by each crosslinking treatment (FIGS. 3A and 3B, respectively). Tangent modulus values began to approach the magnitude order of soft connective tissues. However, the strain at structural failure (at the UTS) decreased in both cases relative to the uncrosslinked samples. DHT increase the modulus and UTS to a greater extent than did the EDC crosslinking. The data represent an average of three samples.

Figure 5:
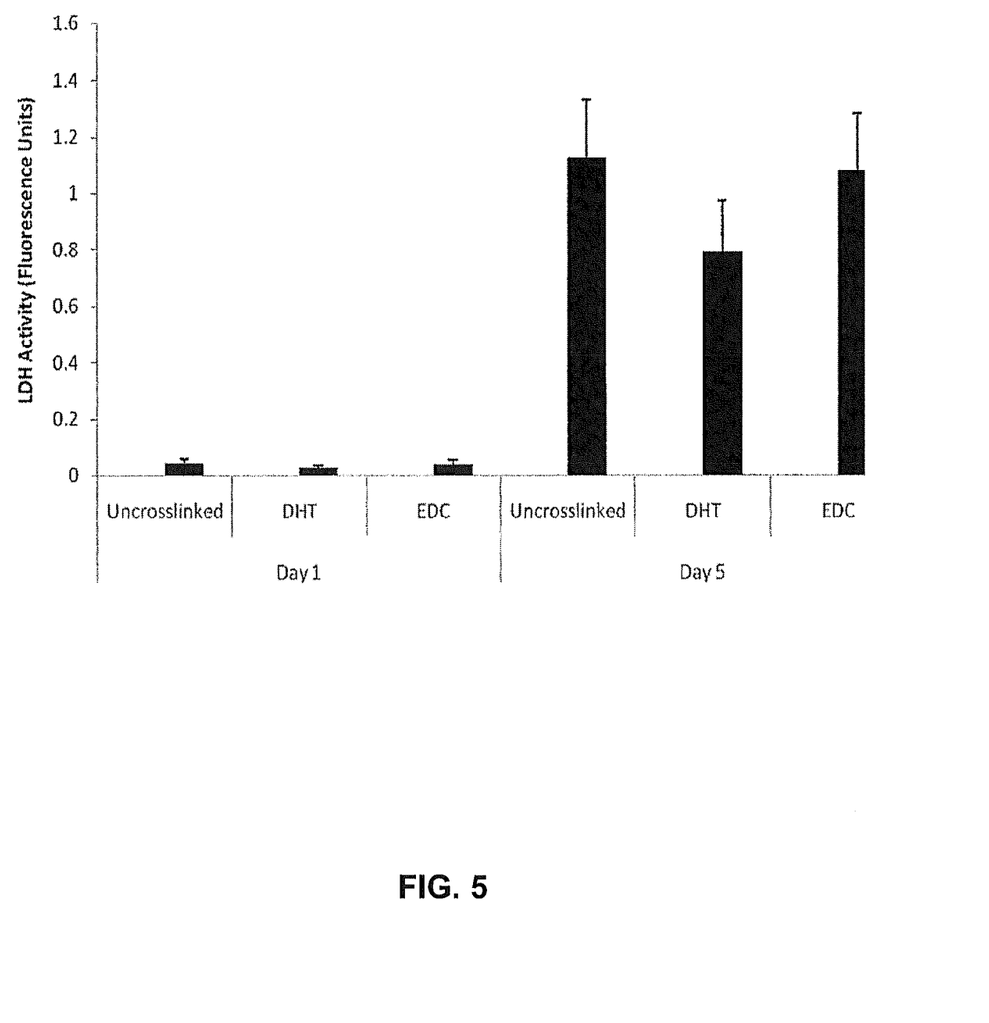
FIG. 5 is a bar graph showing the relative number of ASC on demineralized crosslinked and uncrosslinked cancellous bone scaffolds as determined by lactate dehydrogenase (LDH) for up to five days in culture.
Figure 6A:
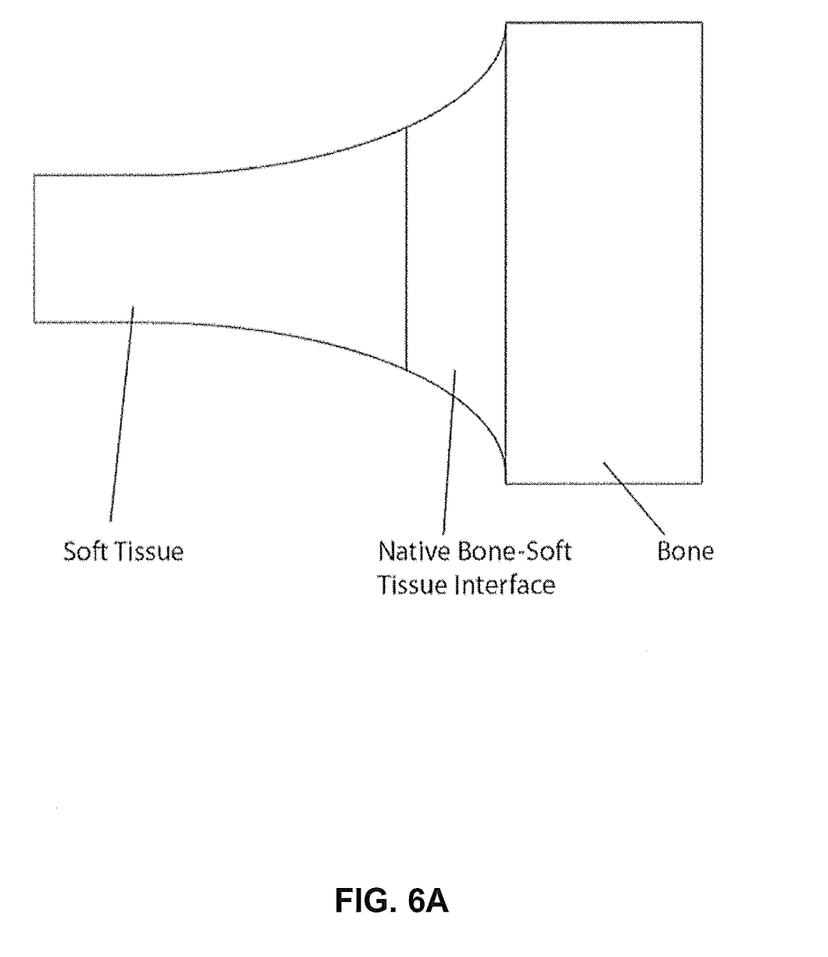
FIG. 6A illustrates the structure of an insertion comprising a native bone-soft tissue interface.
Figure 6B:
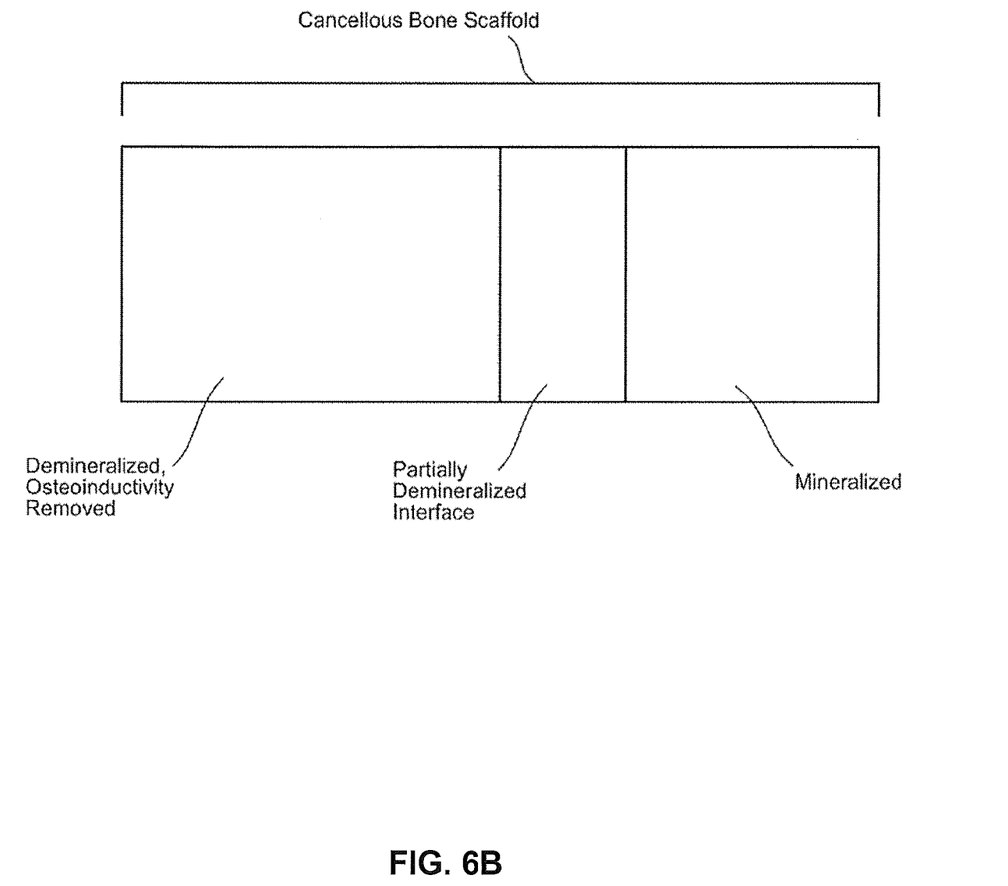
FIG. 6B is a schematic diagram of a cancellous bone scaffold that comprises a contiguous scaffold having a mineralized cancellous bone segment and a demineralized cancellous bone segment and at least one partially demineralized interface between the mineralized segment and the demineralized segment, wherein osteoinductivity has been removed from the demineralized segment and wherein the cancellous bone scaffold is capable of forming an insertion into a calcified bone matrix.

Effect of Cross/Inking on Cell-Biomaterial Interactions:

In increasing the mechanical properties of the collagenous tissues (see above), crosslinking treatments alter the biochemistry of the scaffold. To ensure that the scaffolds were still cytocompatible, cell attachment and proliferation on crosslinked samples were examined and compared to those of untreated samples (FIG. 5). While cell attachment was not adversely affected, proliferation rates on crosslinked samples were less than those on uncrosslinked samples. EDC crosslinked scaffolds displayed a higher rate of proliferation that DHT crosslinked scaffolds.

The invention claimed is:

1. A cancellous bone scaffold configured for insertion into a calcified bone matrix to repair a soft connective tissue interface with a bone, the cancellous bone scaffold comprising a contiguous scaffold having a mineralized cancellous bone segment and a demineralized cancellous bone segment and at least one partially demineralized interface between the mineralized segment and the demineralized segment, the partially demineralized interface comprising 2% to 10% calcium, wherein both the mineralized segment and the demineralized segment are crosslinked, wherein the cancellous bone scaffold has been treated to remove osteoinductivity from at least the demineralized segment, and wherein the cancellous bone scaffold is capable of forming a direct or indirect insertion into a calcified bone matrix.

2. The cancellous bone scaffold of claim 1, wherein the crosslinking increases ultimate tensile strength of the scaffold relative to ultimate tensile strength of an uncrosslinked cancellous bone scaffold.

3. The cancellous bone scaffold of claim 1 wherein the crosslinking comprises at least one of chemical crosslinking and physical crosslinking.

4. The crosslinked cancellous bone scaffold of claim 3, wherein the crosslinking comprises chemical crosslinking obtained by (i) reaction of an amine with an aldehyde, N-hydroxysuccinimide (NHS), isocyanate, epoxide or acrylate, (ii) reaction with a non-selective functional group selected from active esters, epoxides, azide, carbonylimidazole, nitrophenyl carbonate, tresylate, mesylate, tosylate and isocyanate, or (iii) reaction with a carbodiimide, genipin, an aldehyde, an acyl azide, a poly-epoxy compound, butanediol diglycidyl ether, a dye capable of mediating photooxidation, or tannic acid.

5. The crosslinked cancellous bone scaffold of claim 3, wherein the crosslinking comprises physical crosslinking achieved by dehydrothermal crosslinking, exposure to gamma radiation, or exposure to ultraviolet radiation.

6. The cancellous bone scaffold of claim 1 wherein the crosslinked cancellous bone scaffold has greater resistance to proteolytic enzyme degradation than the resistance to proteolytic enzyme degradation of an uncrosslinked cancellous bone scaffold.

7. The cancellous bone scaffold of claim 1, wherein crosslinking does not substantially alter cell attachment to the scaffold relative to cell attachment to an uncrosslinked cancellous bone scaffold.

8. The cancellous bone scaffold of claim 1, wherein the osteoinductivity has been removed from the demineralized segment or the mineralized segment.

9. A method of making the cancellous bone scaffold of claim 1, comprising (a) masking a portion of the bone scaffold by contacting the portion of the bone scaffold with a liquid polymer and permitting the polymer to dry to form a protective coating resistant to demineralization conditions and removable with acetone or ethanol; (b) contacting the bone scaffold of step (a) with a demineralization solution, under conditions and for a time sufficient to at least partially demineralize an unmasked portion of the bone scaffold to comprise 2% to 10% calcium; (c) crosslinking both the mineralized segment and the demineralized segment; and (d) removing osteoinductivity from the cancellous bone scaffold.

10. The method of claim 9, further comprising: (e) washing the bone scaffold following demineralization; and (f) removing the dried polymer.

11. The method of claim 9 wherein the liquid polymer comprises a liquid bandage.

12. The method of claim 9 wherein the liquid bandage comprises a polycyanoacrylate polymer.

13. The cancellous bone scaffold of claim 1, wherein the partially demineralized cancellous bone segment retains 5.36%±1.54% of the mineral present in the cancellous bone following demineralization.

* * * * *